United States Patent [19]
Danzik et al.

[11] Patent Number: 5,837,171
[45] Date of Patent: Nov. 17, 1998

[54] METHOD OF ENCAPSULATING AND STERILIZING WASTE PRODUCTS FOR DISPOSAL OR REUSE

[76] Inventors: Dennis M. Danzik, 360 Arroyo Grande Blvd., #818, Henderson, Nev. 89014; R. Lindsey Dalley, 5060 Moapa Valley Blvd., Logandale, Nev. 89021

[21] Appl. No.: 711,485

[22] Filed: Sep. 10, 1996

Related U.S. Application Data

[60] Provisional application No. 60/003,664, Sep. 11, 1995.

[51] Int. Cl.⁶ .................................................... B29C 41/04
[52] U.S. Cl. ............................ 264/45.7; 264/37; 264/54; 264/310; 264/311
[58] Field of Search .............................. 264/37, 310, 311, 264/45.7, 54

[56] References Cited

U.S. PATENT DOCUMENTS

| | | |
|---|---|---|
| 4,234,632 | 11/1980 | Lubowitz . |
| 4,717,510 | 1/1988 | James . |
| 4,905,916 | 3/1990 | Sorwick et al. . |
| 4,975,224 | 12/1990 | Pringle . |
| 5,008,045 | 4/1991 | Manchak ................................. 264/311 |
| 5,075,045 | 12/1991 | Manchak ................................. 264/311 |
| 5,277,869 | 1/1994 | Glazer et al. . |
| 5,322,603 | 6/1994 | Kameda et al. . |
| 5,401,444 | 3/1995 | Spinello .................................. 264/0.5 |

*Primary Examiner*—James Derrington
*Attorney, Agent, or Firm*—Quirk & Tratos

[57] ABSTRACT

A method of encapsulating and sterilizing waste material is disclosed. Medical waste is deposited inside of a mold. When full, the mold is charged with plastic and one of several reactants. The mold is then heated while rotated biaxially. The heat simultaneously sterilizes the waste and causes the charging materials to expand and envelop the waste, encapsulating it. The mold is then cooled while spinning biaxially, forming a hollow brick of solidified, encapsulated material in the mold. The brick of material is removed and pulverized into granules. The pulverized material is separated and readied for recycling.

9 Claims, 7 Drawing Sheets

METHOD OF ENCAPSULATING AND STERILIZING WASTE PRODUCTS FOR DISPOSAL OR REUSE

CROSS-REFERENCE TO RELATED APPLICATION

Applicants claim the benefit of an earlier filed provisional patent application entitled "Method of Encapsulating and Sterilizing Waste Products for Disposal or Reuse" filed Sep. 11, 1995, Ser. No. 60/003,664.

FIELD OF THE INVENTION

The present invention relates to a method for containing waste products, encapsulating them, sterilizing them, and recycling the end product.

BACKGROUND OF THE INVENTION

Disposal of medical waste products is a significant societal issue. Medical facilities, morgues, veterinaries and similar facilities generate tons of medical waste product daily. This waste often includes "sharps," items such as needles, scalpels, and razors which can cut or puncture tissue and other material, and "red-bag" or blood contaminated waste such as pads, sponges, and swabs. This waste is often classified as "contaminated" or "hazardous" under environmental laws, such that it can not simply be disposed of in conventional manners.

Presently, several methods exist for disposing of this waste, none of which are completely acceptable. One commonly used method involves storing the materials in a container and then heating the container including waste in an oven in an attempt to sterilize the waste. This process is called "autoclaving." Afterwards, the waste, or container including waste, is disposed of in a conventional manner, such as by discarding it in a dump.

The autoclaving process has several drawbacks. First, the temperature at which the heating process occurs is often too low to sterilize the waste. If the heating temperature is raised to achieve sterilization, the waste can catch fire or may melt in the oven, making it difficult to remove.

Further, once the autoclaving process is completed, the waste is simply placed in landfills, etc. If the container is opened, either intentionally or unintentionally, the contents of the same are accessible. Thus, waste, including "sharps," are accessible to and can injure those who later encounter them. Moreover, the sharps items are not destroyed, and can be retrieved by such parties and reused.

Several other processes are disclosed in the literature for neutralizing or sterilizing waste, all of which are unacceptable. For instance, some processes use hot water or other liquids to sterilize materials. These processes create contaminated liquids, which in and of themselves must then be treated before being disposed of.

SUMMARY OF THE INVENTION

The present invention is a method and related apparatus for encapsulating and sterilizing waste material and converting it into a usable end-product. A user deposits waste in a mold. Preferably, the mold comprises a hollow top shell member and bottom shell member coupled to one another. An orifice is located in a top surface of the top shell, through which a user drops waste material into the interior chamber of the mold.

When the mold is full, the user inserts a charging probe into the interior of the mold. A mixture of thermoplastic and an expansive reactant is charged into the mold. The user then removes the charging probe and inserts a sterilization probe. The sterilization probe is hollow and contains a sterilizing indicator such as a heat indication or baseline culture strip.

The user heats the charged mold in a chamber while simultaneously spinning the mold biaxially or by gyration. During the heating and spinning process, the reactants cause the charged material to expand, envelop and encapsulate the waste material. At the same time, the heat causes much of the waste to melt, evaporate, or boil away. Heating also sterilizes the waste material. Spinning the mold urges, by centripetal force, the heavier waste material, metal and plastic to the outside of the mold, forming a hollow brick of encapsulated, sterilized material.

Once encapsulation is complete, the mold is cooled while spinning biaxially or gyrating the mold. After the mold is removed from the machine, the sterilization probe is opened and a heat indication strip or culture strip is removed for observation and testing to confirm sterilization. The solidified, treated brick is then removed from the mold.

The user preferably granulates the brick of material. Afterwards, the user may dispose of the material or recycle it. Preferably, the material is recycled after metal and plastic material has been separated. The plastic material is pulverized, cleaned, and pelletized for use in other applications.

Further objects, features, and advantages of the present invention over the prior art will become apparent from the detailed description of the drawings which follows, when considered with the attached figures.

DETAILED DESCRIPTION OF THE PREFERRED EMBODIMENT

Figure 1:
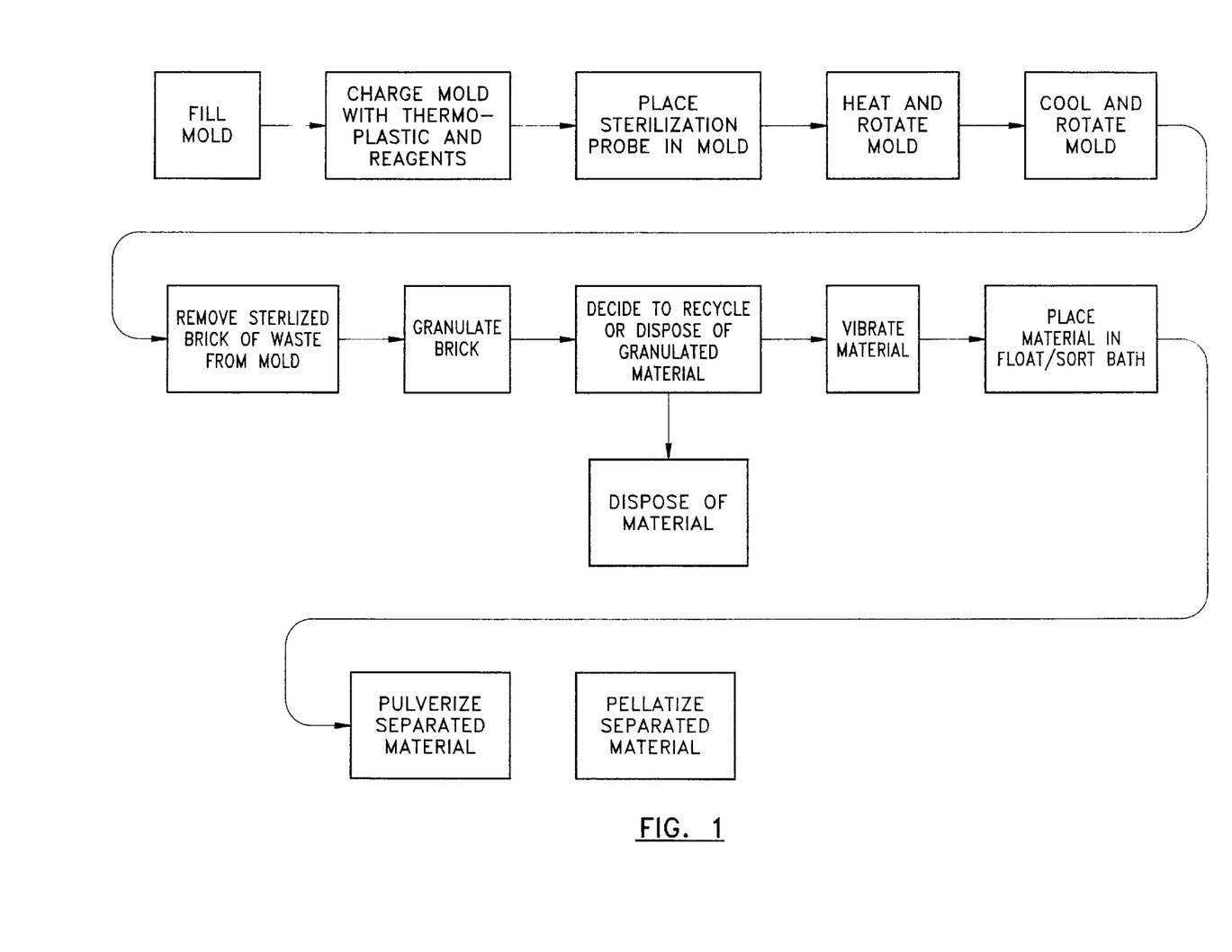
FIG. 1 is a block diagram illustrating the steps of encapsulating and sterilizing waste in accordance with the method of the present invention.

FIG. 1 is a block diagram illustrating the steps of the method of encapsulating and sterilizing waste in accordance with the present invention. In general, the method comprises the steps of filling a mold with waste, charging the mold with thermoplastic and reactant, heating the mold containing the waste and charging materials in a chamber from between 250 to 1200 degrees Fahrenheit while spinning it biaxially or gyrating the mold to sterilize the waste and encapsulate it in plastic, cooling the mold while the mold is still spinning (or gyrating) to form a hollow brick of encapsulated sterilized waste material, removing the brick of material from the mold, and processing the brick of material for disposal or recycling.

In additional steps illustrated in FIG. 1, the brick may either be disposed of or recycled. If recycled, the material is preferably granulated into pellets and separated by vibration, float/sink baths, magnetic separation, air separation, electrostatic separation, and/or extrusion. Metal material is separated for recycling. Plastic material is preferably pulverized, cleaned and pelletized for use in other applications.

FIGS. 2–5 and 7 illustrate a preferred embodiment of a mold 20 for use in the method of the present invention. In general, the mold 20 comprises a container comprising mating top and bottom shell members 22,24. When engaged, the shell members 22,24 define an inner storage cavity 26. While the mold 20 is preferably made of cast metal, it may be constructed from any temperature resistant material such as plastic, silicones, aluminum, copper, steel, nickel, ceramic, or glass.

Overall, the mold 20 is rectangular in shape, being about 24 inches long, 11 inches wide, and 12 inches deep. The top and bottom shell members 22,24 have approximately the same outer dimensions of 24 inches length, 11 inches width, and 6 inches depth. An approximately 1.5 inch wide flange 28 extends circumferentially around a bottom portion of the top shell member 22, and a similar mating flange 30 extends around a top portion of the bottom shell member 24.

A number of bores 32 are spaced around the flange 28 on the top shell member 22. A number of similar aligned bores 34 are spaced around the flange 30 on the bottom shell member 24. Preferably, one or more bolts 36 pass through the mating bores 32,34 to securely hold the top and bottom shell members 22,24 together.

Figure 2:
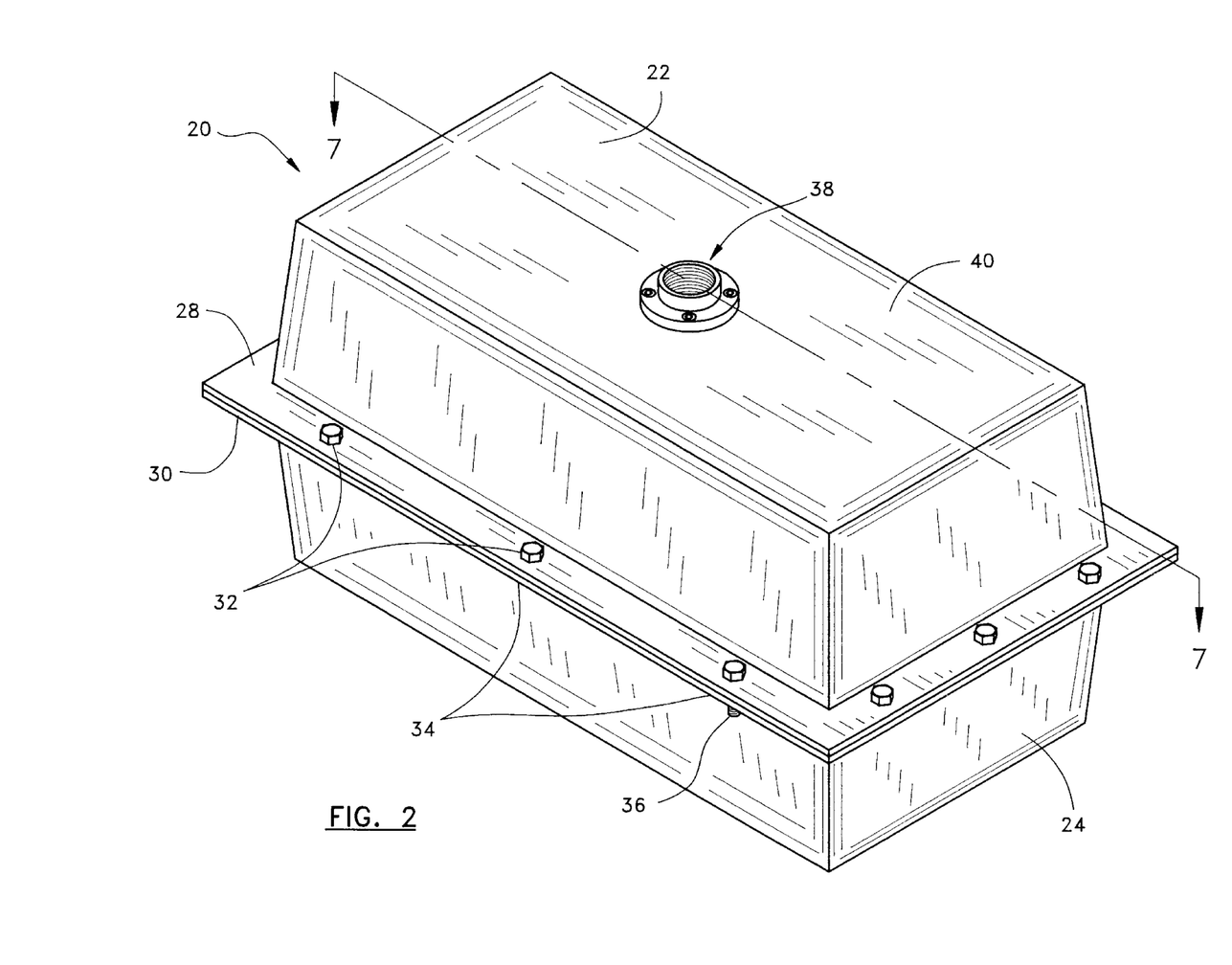
FIG. 2 is a perspective view of a mold for use in the method of the present invention.
Figure 3:
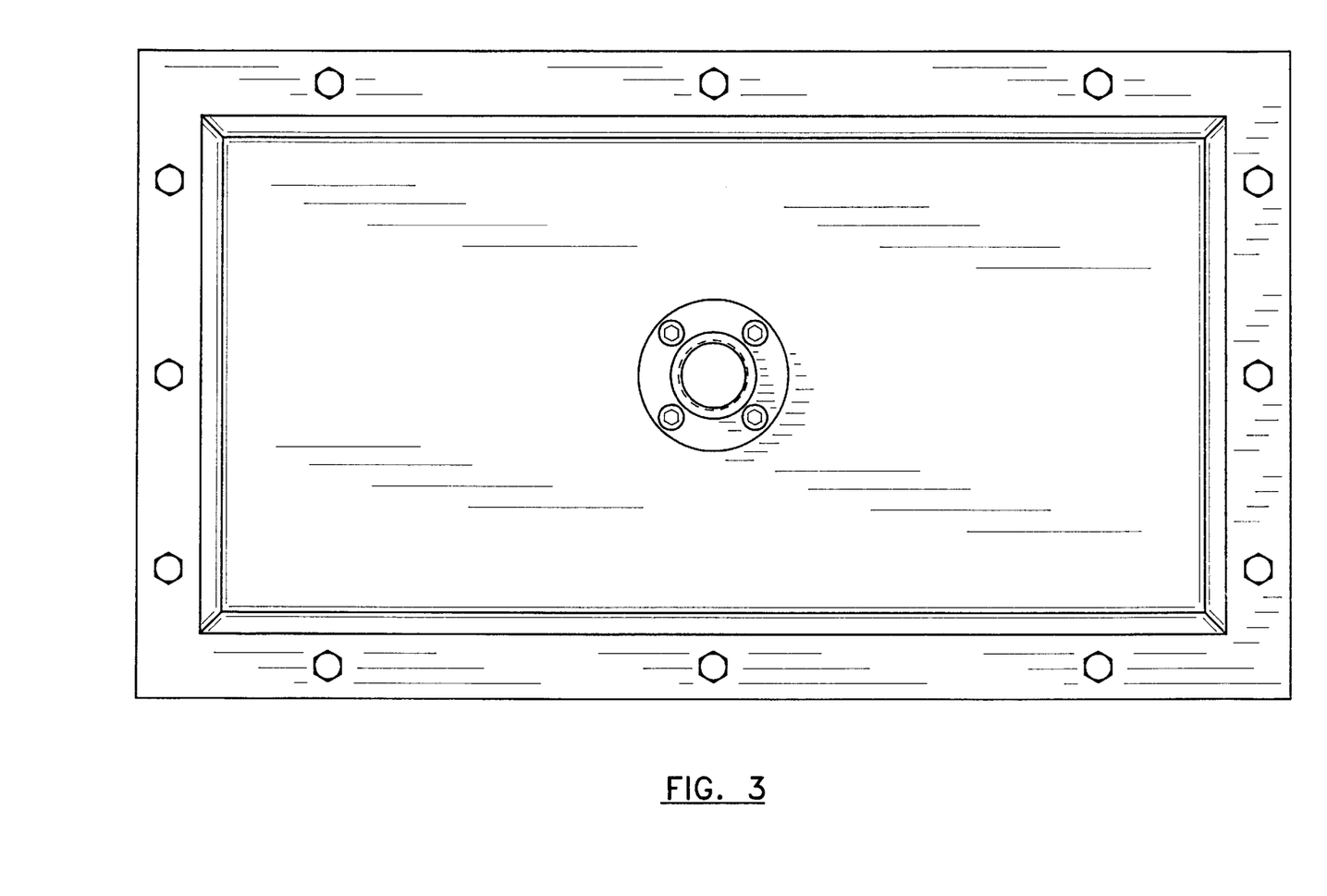
FIG. 3 is a top view of the mold of FIG. 2.
Figure 4:
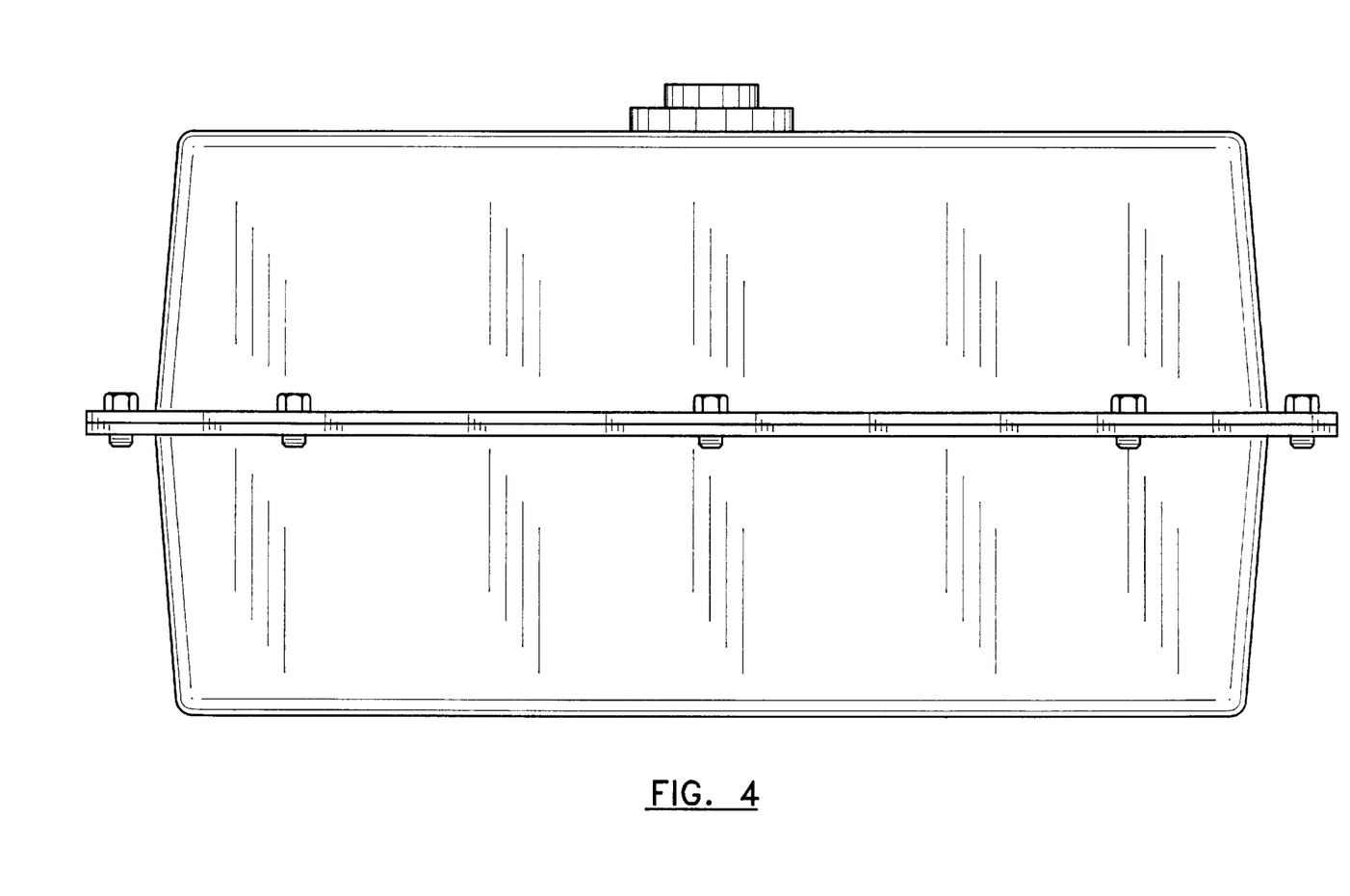
FIG. 4 is a side view of the mold of FIG. 2.
Figure 5:
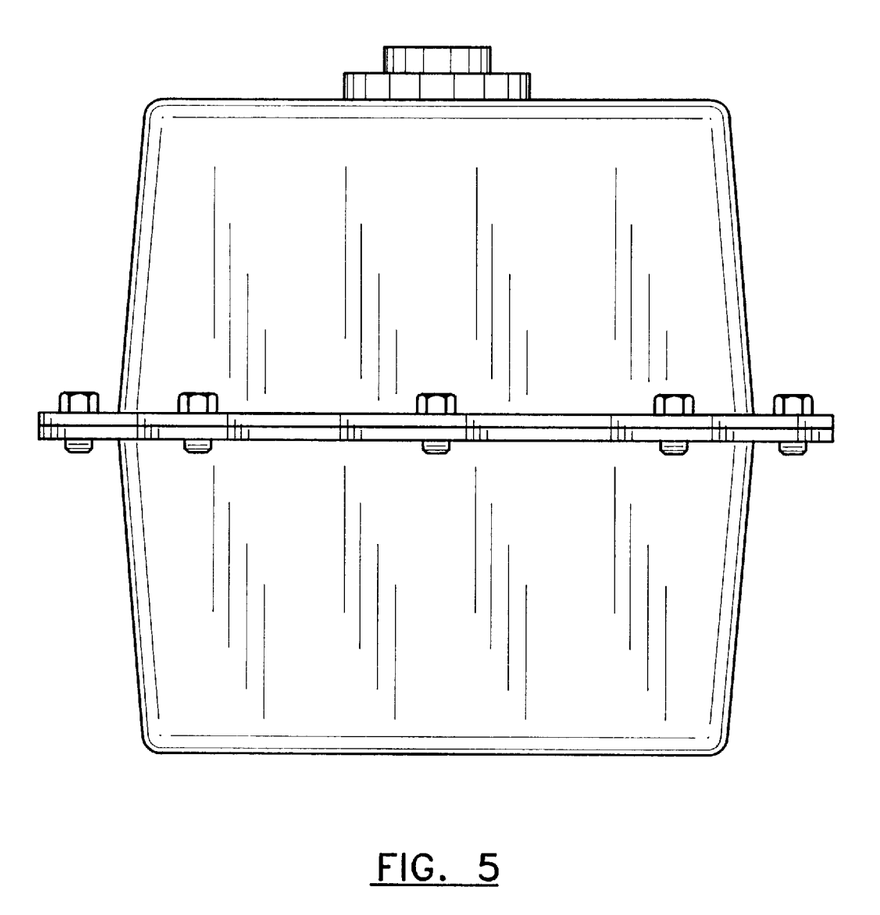
FIG. 5 is a an end view of the mold of FIG. 2.

An orifice 38 is located in a top surface 40 of the top shell member 22. The orifice 26 is a circular opening of about 0.5–5.0 inches in diameter through which users drop waste material into the mold, through which a charging probe 44 (see FIG. 8) passes when the mold is charged, and through which a sterilization probe 42 is positioned when the mold is being heated and cooled.

An orifice insert 46 (see FIGS. 6 and 7) is located in the orifice 38. The insert 46 is preferably annular in shape, having a central passage 48 therethrough. The insert 46 has a top surface 50, bottom surface 52, inner surface 54, and outer surface 56. The insert 46 comprises a cylindrical neck 58 and a flange 60 extending circumferentially around the neck. Threads 64 are situated on the inner surface 54 of the insert 46.

Figure 6:
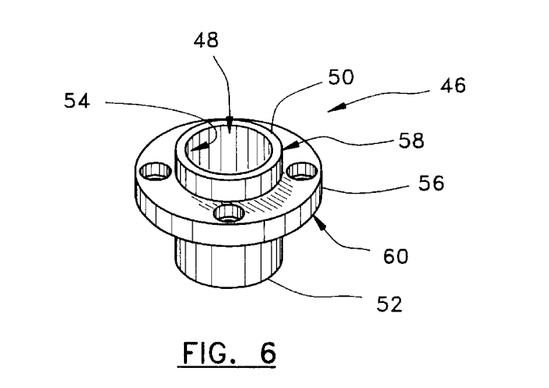
FIG. 6 is a perspective view of an orifice insert of the present invention.
Figure 7:
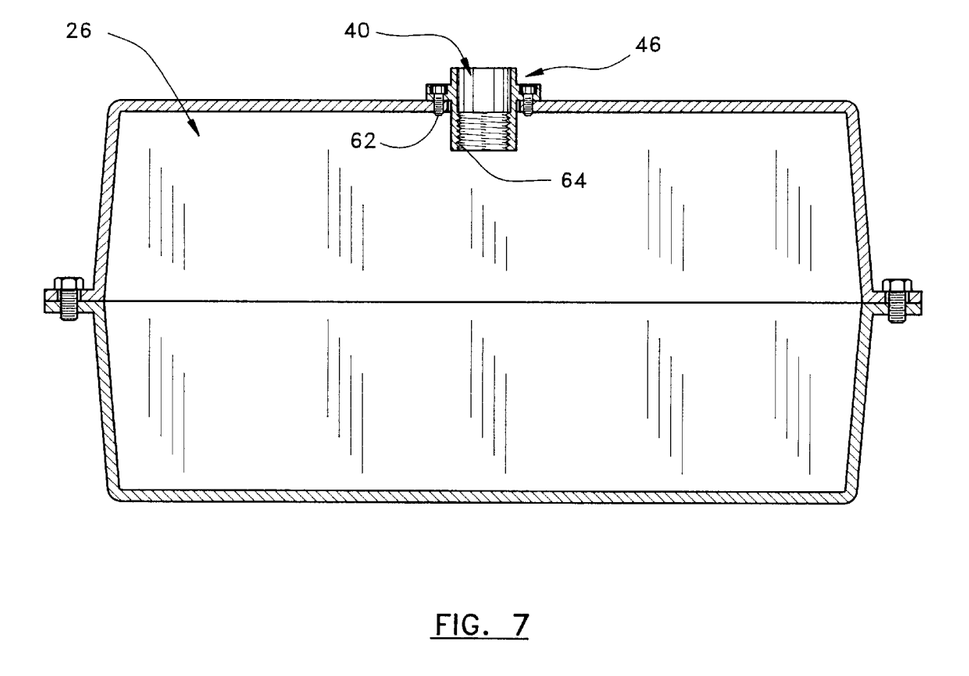
FIG. 7 is a cross-sectional view of the mold of FIG. 2 through line 7—7.

The flange 60 is positioned down from the top surface 50 of the insert 40. The flange 60 extends outwardly from the neck 58. Preferably, four threaded pins 62 (only two of which shown) extend downwardly from the flange 60.

Preferably, the insert 46 is attached to the top surface 40 of the top shell member 22. In particular, the pins 62 are preferably threaded into the top shell member 22. The insert 46 may be attached to the mold 20 or may be fashioned integrally with the top shell member 22.

Figure 8:
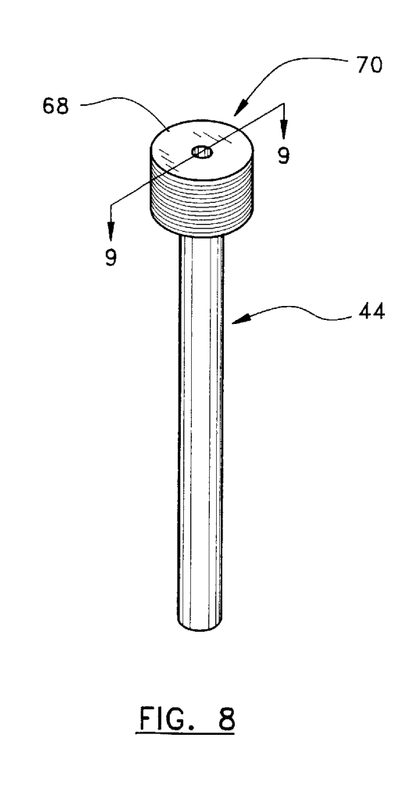
FIG. 8 is a perspective view of a changing probe of the present invention.
Figure 9:
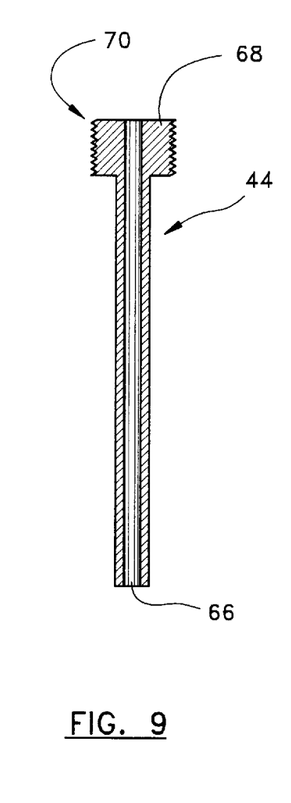
FIG. 9 is a cross-sectional view of the probe of FIG. 8 through line 9—9.

Referring now to FIGS. 8 and 9, the charging probe 44 is used to charge the waste laden mold 20 with thermoplastics and reactants. The probe 44 comprises an elongate cylindrical member having a central passage 66 through the length thereof. A head 68 is located at a top end 70 of the probe 44. The head 68 has a threaded exterior which is sized for mating engagement with the threads 64 on the interior surface 54 of the insert 46. The particular size and length of the probe 44 varies dependent on the size of the mold 20 it is used with. For example, when used with the mold 20 described above, the probe 44 is about 8–10 inches long. Preferably, tubing or similar means are attached to the central passage 66 at the top end 70 of the probe, enabling a user to inject thermoplastic material and reactants through the probe into the mold 20 for charging thereof.

Figure 10:
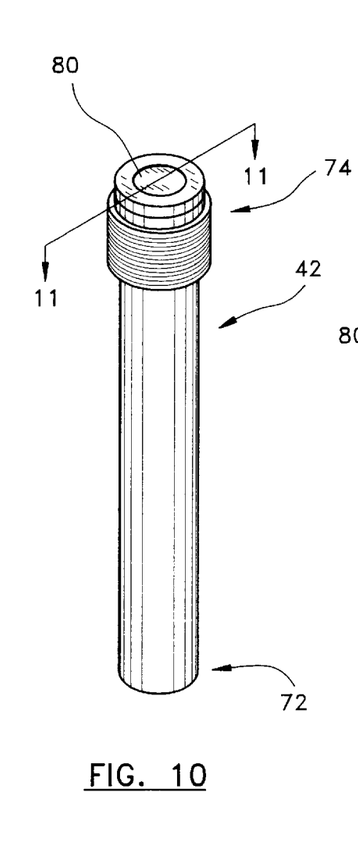
FIG. 10 is a perspective view of a sterilization probe of the present invention.
Figure 11:
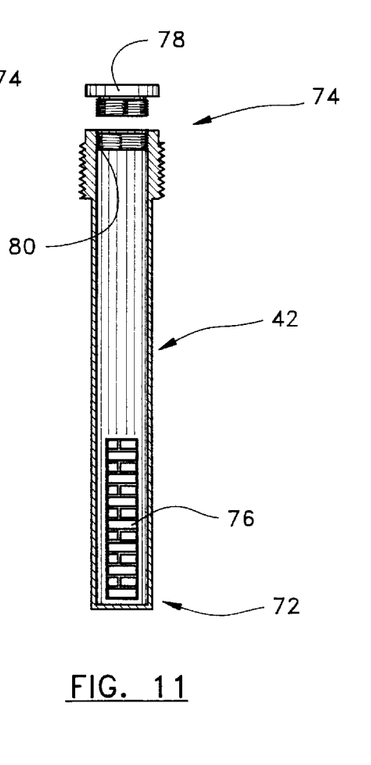
FIG. 11 is a cross-sectional view of the probe of FIG. 10 through line 11—11.

Referring now to FIGS. 10 and 11, the sterilization probe 42 is an elongate cylindrical body having a first closed end 72 and a second open end 74. Again, the size of probe 42 used may vary dependent upon the size of mold 20 it is used with. For the mold 20 described above, the probe 42 is about 8–10 inches long to locate the terminal end thereof centrally within the mold 20. The probe 42 is externally threaded and sized at the second end 74 for mating engagement with the threads 64 on the interior surface 54 of the insert 46 on the mold 20.

The sterilization probe 42 has a hollow interior space into which a sterilization indicator 76, such as a heat indicator strip, sterility indication strip, or a baseline bio-medical laboratory culture is inserted. In order to seal the second open end 74 of the probe 42 during use, so that interior space is not contaminated by outside air, a plug 78 is selectively locatable in the second end 74. The plug 78 is threaded on an outer surface for mating engagement with threads 80 located on the inside of the probe 42.

The method of the present invention is as follows. Referring again to FIG. 1, a user fills the mold 20 with medical waste, including sharps and red bag waste. The user drops the waste material through the orifice 40 in the top surface 40 of the mold 20. A user may place a lid over the orifice 40 to keep the waste enclosed in the mold 20 except when the user wishes to insert waste through the orifice.

Once the inner storage space 26 of the mold 20 is full, the mold 20 and its contents are sterilized in accordance with the method of the present invention. First, a user engages the charging probe 44 with the insert 46. In particular, the user inserts the probe 44 through the orifice 40 and threadingly engages the head 68 of the probe 44 with the threads 64 on the interior surface 54 of the insert.

The user then connects the probe 44 to a charging line or similar apparatus which supplies the charge. The user then "charges" or fills the mold with a mixture of plastic and other reactants. Preferably, the charge comprises polyethylene and one or more reactants which, when heated, expand or cause the thermoplastic to expand in volume. Preferably, these reactants may be selected from Azodicarbonomide, modified Azodicarbonomide, p-Toluene sulfonyl semicarbazide, p,p-Oxybis benzene sulfonyl hydrazine, and p-Toluene sulfonyl hydrazide.

With the mold 20 charged, the user removes the charging probe 44 and inserts means for monitoring the sterilization process within the mold. Preferably, this means comprises the sterilization probe 42 with a baseline culture strip 76 including a suitable active culture disposed therein or thereon. Alternatively or additionally a thermal indicator may be disposed in the sterilization probe 42 to sense and record the temperature achieved during sterilization. The user inserts the sterilization probe 42 into the mold 20 through the orifice 40 and mates the threads on the outside of the probe 42 with the threads 64 on the interior surface 54 of the insert 46. The user inserts the culture strip 76, and places the plug 78 over the open second end 74 of the probe 42.

With the sterilization probe 42 in place, the mold 20 is heated while subjecting the mold 20 to centripetal forces by spinning or gyrating the mold 20. Preferably, the mold 20 is located in a heated chamber and spun biaxially by suitable means, that is to say the mold is spun about two axis at the same time. The exact temperature to which the mold 20 is heated, and thus the time the mold 20 is spun in the chamber and the temperature in the chamber, may differ depending on the type of waste, size of the mold, performance of the reactants and similar factors. The mold 20 must be heated to a sufficiently high temperature, and for a long enough time that the waste material within the mold 20 is sterilized. In general, however, the mold 20 (and its contents) will generally be heated to around 250 to 1200 degrees Fahrenheit, depending on the type of waste, reagents, and plastic charge.

The heat is applied and the mold 20 spun long enough that the reactants in the charge react, causing the charge material to expand, envelop and encapsulate the waste material within the mold 20. The sterilization indicator 76 is used to confirm that the mold 20 was heated sufficiently to sterilize the waste within the mold 20. Post-heating analysis of the baseline culture determines whether sterilization has been achieved. Additionally examination of the thermal sensor determines whether temperatures have been obtained during heating to confirm sterilization.

During the heating and spinning process, the thermoplastic material and waste are spun to the outside of the container, forming a brick of material with a hollow core. Some waste material (such as plastic items) melt, reducing the volume of the waste. Fluid waste (air, water, and similar substances) is vaporized, migrates to the hollow center of the mold and, if the pressure is sufficient, vents from the mold 20 into the chamber.

After heating, the mold 20 continues to spin (preferably biaxially) the mold 20 in the chamber in a cooling process. In this step, the mold 20 and its contents are spun while the temperature of the mold is brought back down to room temperature.

Once cooled, the mold 20 contains a hollow solid brick of encapsulated and sterilized waste material. At this time, the brick of material is removed from the mold 20, along with the sterilization probe 42 and culture and/or thermal sensor.

The material is then ready for disposal or recycling. The brick of material may be recycled or disposed of without the threat of contamination, nor the threat that sharps or similar materials will be accessed. For example, if the user disposes of the brick of material by depositing it in a landfill, a scavenger can not remove the waste (such as syringes and the like), since the waste is encapsulated within the durable plastic material. Any attempted removal would be difficult and likely damage any sharps, e.g. needles. This fact, along with the fact that the waste was sterilized during the heating process, also ensures that no contamination will occur if the brick of material is disposed of in this manner.

As illustrated in FIG. 1, however, it is preferred that the brick of material be shredded or granulated, such as with a knife-style granulator, for recycling.

Once granulated, the material is preferably separated, such as by use of a float/sink bath, one or more vibrators, electrostatic or magnetic separation, air separation, extrusion, or other means known in the art. Preferably, the granulated material is first separated in a vibratory, magnetic separation process to separate metal and plastic elements. Once vibrated, the plastic material is preferably further separated in at least one float/sink or "floatation" bath.

In the floatation baths, remaining metal pieces sink to the bottom for collection. Plastic elements can also be separated from one another in one or more float/sink baths, the number of baths dependent on the degree of separation required.

Once separated, the plastic material can be pulverized, cleaned, pelletized for resale or for use in the formation of other products. Metal material can be recycled and reused as well.

While the above represents the preferred embodiment of the present invention, it is understood that many variations of the method and apparatus are possible without deviating from the scope of the invention.

The particular size and shape of the mold may vary depending on the type and amount of waste material which is to be disposed of. The mold may also be formed in one piece. Such is especially advantageous if the mold is made of plastic and simply granulated and recycled along with the brick of sterilized waste material formed therein.

The size of the orifice 40 (and thus the interior diameter of the insert 46) is chosen to allow a user to pass most waste items into the mold. On the other hand, it may be desirable to limit the size of the orifice somewhat, so as to prevent others from accessing the interior of the mold and removing waste items.

It will be understood that the above described arrangements of apparatus and the method therefrom are merely illustrative of applications of the principles of this invention and many other embodiments and modifications may be made without departing from the spirit and scope of the invention as defined in the claims.

We claim:

1. A method of encapsulating and sterilizing waste comprising:

charging a mold containing said waste with a plastic material and at least one reactant selected from the group consisting of: Azodicarbonomide, modified Azodicarbonomide, p-Toluene sulfonyl semicarbazide, p,p-Oxybis benzene sulfonyl hydrazine, and p-Toluene sulfonyl hydrazine, said reactant adapted to cause the plastic material to expand when heated;

heating the mold, said heating causing the plastic and charged material to expand and envelop and sterilize the waste material;

spinning the mold to impose centripetal force on the mold, waste material and charging material;

cooling the mold and forming a solid brick of encapsulated waste material in said mold.

2. A method of encapsulating and sterilizing waste comprising:

charging a mold containing said waste with a plastic material and a reactant, said reactant adapted to cause the plastic material to expand when heated;

inserting a sterilization probe into an orifice in said mold;

heating the mold to cause the charging material to expand, envelop, encapsulate and sterilize the waste material;

spinning the mold to impose centripetal force on the mold, waste material and charging material; and cooling the mold and forming a solid brick of encapsulated waste material in said mold.

3. The method of claim 2 including locating a sterilization indicator in said probe.

4. The method of claim 2 including locating a culture strip in said probe.

5. A method of containing and sterilizing waste material comprising the steps of:

locating the waste material in an interior chamber of a mold;

charging said interior chamber of said mold with a plastic material and at least one expansive reactant;

inserting means for confirming sterilization of said waste material into said mold;

heating said mold to cause the charging materials to expand and envelop and sterilize said waste;

spinning the mold to impose centripetal force on the mold; and cooling said mold and forming a solid brick of encapsulated waste material in said mold.

6. The method of claim 5, further comprising the steps of removing said brick of encapsulated waste material from said mold and granulating said brick of encapsulated waste material.

7. The method of claim 5, wherein said spinning step comprises rotating said mold biaxially.

8. The method of claim 5, wherein said mold is rotated during said heating and cooling steps.

9. The method of claim 6, further comprising the step of recycling the granulated brick of encapsulated waste material.

* * * * *